(12) United States Patent
Wataya et al.

(10) Patent No.: US 8,927,596 B2
(45) Date of Patent: Jan. 6, 2015

(54) ANTISCHISTOSOMAL AGENT

(71) Applicant: National University Corporation Okayama University, Okayama (JP)

(72) Inventors: Yusuke Wataya, Okayama (JP); Hye-Sook Kim, Okayama (JP); Akiko Hiramoto, Okayama (JP); Akira Sato, Okayama (JP); Nobuo Ota, Tokyo (JP); Takashi Kumagai, Tokyo (JP); Rieko Shimogawara, Tokyo (JP); Toshie Taniguchi, Tokyo (JP)

(73) Assignee: National University Corporation Okayama University, Okayama (JP)

( * ) Notice: Subject to any disclaimer, the term of this patent is extended or adjusted under 35 U.S.C. 154(b) by 20 days.

(21) Appl. No.: 13/871,061

(22) Filed: Apr. 26, 2013

(65) Prior Publication Data

US 2013/0245108 A1 Sep. 19, 2013

Related U.S. Application Data

(63) Continuation of application No. 13/001,676, filed as application No. PCT/JP2009/061698 on Jun. 26, 2009, now abandoned.

(30) Foreign Application Priority Data

Jul. 1, 2008 (JP) ................................ 2008-172663

(51) Int. Cl.
| | |
|---|---|
| *A01N 43/02* | (2006.01) |
| *A61K 31/335* | (2006.01) |
| *C07D 319/00* | (2006.01) |
| *C07D 321/00* | (2006.01) |
| *C07D 323/00* | (2006.01) |
| *A61K 31/357* | (2006.01) |
| *C07D 325/00* | (2006.01) |

(52) U.S. Cl.
CPC ............ *C07D 323/00* (2013.01); *A61K 31/357* (2013.01); *C07D 325/00* (2013.01)
USPC ............................ 514/450; 549/333; 549/347

(58) Field of Classification Search
USPC .................................... 514/450; 549/333, 347
See application file for complete search history.

(56) References Cited

U.S. PATENT DOCUMENTS

| | | | |
|---|---|---|---|
| 6,486,199 | B1 | 11/2002 | Vennerstrom et al. |
| 6,825,230 | B2 | 11/2004 | Vennerstrom et al. |
| 2005/0142204 | A1 | 6/2005 | Lotter et al. |
| 2011/0172445 | A1 | 7/2011 | Wataya et al. |

FOREIGN PATENT DOCUMENTS

JP 2000-229965 8/2000

OTHER PUBLICATIONS

Translation of International Search Report issued in corresponding International Patent Application No. PCT/JP2009/061698 dated Aug. 18, 2009 (2 pages).
Taniguchi et al., Yuki Kagobutsu o Mochiita Ko Juketsu Kyuchu Chiryoyaku no Tansaku, Annual Meeting of the Japanese Society of Parasitology Program Shorokushu, Feb. 23, 2007, vol. 76, p. 34 (2 pages).
Keiser et al., "Mefloquine—An Aminoalcohol with Promising Antischistosomal Properties in Mice," PLoS Neglected Tropical Diseases, Jan. 2009, vol. 3, e350, pp. 1-11 (11 pages).
Laurent et al., "Synthesis of "Trioxaquantel" Derivatives as Potential New Antischistosomal Drugs," European Journal of Organic Chemistry, 2008, vol. 2008, No. 5, pp. 895-913 (20 pages).
Renslo et al., "Drug discovery and development for neglected parasitic diseases," Nature Chemical Biology, Dec. 2006, vol. 2, No. 12, pp. 701-710 (11 pages).
"Schistosomiasis," Infectious Disease Surveillance Center, National Institute of Infectious Diseases, Week 41 of 2006 (Sep. 10-15) (in Japanese with English translation attached) (13 pages).
Product Monograph, "Biltricide" (Praziquantel) Tablets Antihelminthic, Bayer, Inc., revised Nov. 30, 2007, pp. 1-18 (18 pages).

*Primary Examiner* — Kendra D Carter
(74) *Attorney, Agent, or Firm* — Kilyk & Bowersox, P.L.L.C.

(57) ABSTRACT

An object of the present invention is to provide a novel antischistosomal agent, and more specifically, to provide a novel drug capable of inhibiting a growth of schistosomes in vivo to prevent development of liver dysfunction due to eggs of the schistosomes in the case of infection with the schistosomes. The novel antischistosomal agent includes as an active ingredient a peroxide derivative. Specifically, the novel antischistosomal agent includes as an active ingredient a peroxide derivative represented by the general formula (I):

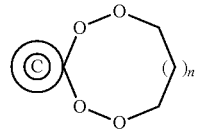

Formula (I)

where C represents an alicyclic hydrocarbon ring group which may be substituted, and n represents an integer of 1 to 6.

20 Claims, 4 Drawing Sheets

ANTISCHISTOSOMAL AGENT

This application is a continuation of U.S. patent application Ser. No. 13/001,676, which in turn is a National Stage Application of PCT/JP2009/061698, filed Jun. 26, 2009, which claims priority to JP 2008-172663, filed Jul. 1, 2008.

TECHNICAL FIELD

The present invention relates to a novel compound useful for the prophylaxis and treatment of schistosomiasis, and more specifically, to a novel drug capable of killing schistosomes, and when the schistosomes cannot be killed, inhibiting the growth of the schistosomes depending growth stages in vivo to prevent the development of liver dysfunction caused by worms' eggs in the case of infection with the schistosomes.

The present application claims the priority of JP 2008-0172663, which is hereby incorporated by reference.

BACKGROUND ART

Schistosomiasis is a disease caused by the parasitism of adult schistosomes in the veins and is broadly classified into urogenital schistosomiasis and intestinal schistosomiasis. An example of the urogenital schistosomiasis is *schistosomiasis haematobia* (pathogen: *Schistosoma haematobium*) and examples of the intestinal schistosomiasis include *schistosomiasis mansoni* (pathogen: *S. mansoni*), *schistosomiasis mekongi* (pathogen: *S. mekongi*), and *schistosomiasis intercalatum* (pathogen: *S. intercalatum*) as well as *schistosomiasis japonica* (pathogen: *S. japonicum*). Infection of humans with schistosomes occurs when the humans go into fresh water, for example, a river, a lake, or a marsh. The World Health Organization estimates that 200,000,000 people suffer from the disease worldwide, and the number of people died of severe complications associated with the disease is estimated to be annually 20,000 or 200,000, which varies from report to report. *Schistosomiasis haematobia* is distributed in Middle East, wide range of areas in Africa including Madagascar, and Mauritius, and *schistosomiasis mansoni* is distributed in, for example, the Arabian Peninsula, most of African countries located north of the equator (Egypt, Libya, Sudan, Somalia, Mali, and Senegal), Mauritius, Brazil, some of various Caribbean countries, Surinam, and Venezuela. *Schistosomiasis japonica* is distributed in, for example, the Yangtze valley in China, Philippines, and the island of Sulawesi in Indonesia, *schistosomiasis mekongi* is distributed in the Mekong river basin in Cambodia and Laos, and *schistosomiasis intercalatum* is locally distributed in West and Central Africa.

Also in Japan, there were several areas endemic for *schistosomiasis japonica* in the past. However, the execution of an eradication project including land-use alteration and measures for intermediate hosts as well as community education and mass examination has contributed to a drastic decrease in the number of infected people. As a result, there has been no report on people newly infected with *Schistosoma japonicum* since 1976 in Japan.

Information about the kinds of pathogens, life cycles of pathogens, clinical symptoms of infectious diseases, pathological diagnosis, and the like for schistosomiasis is described in detail in the homepage of Infectious Disease Surveillance Center, National Institute of Infectious Diseases (http://idsc.nih.go.jp/idwr/kansen/k06/k06_41/k06_41.html) (Non Patent Literature 1).

s for measures against schistosomiasis, instructions for the prophylaxis of infection have been made to avoid going barefoot into the habitat of shellfish as an intermediate host for schistosomes, i.e., a river, a pond, etc., and besides, praziquantel (Bayer Yakuhin) is commercially available as a magic bullet (Non Patent Literature 2). The treatment of schistosomiasis is basically conducted by single-dose administration of praziquantel at 40 mg/kg. It is said that schistosomiasis is cured by the treatment inmost cases. Acute symptoms (e.g., abdominal pain, diarrhea, mucous and bloody stool, fever, and cough) of schistosomiasis are known as Katayama's fever, and when not being treated, the symptoms are basically relieved and become chronic. Even when Katayama's fever is relieved by the administration of praziquantel, praziquantel is not effective against immature schistosomes, and is therefore recommended to be administered again after 3 months. Praziquantel is also said to have no prophylactic effect. Meanwhile, Non Patent Literature 1 also describes that it has been reported that artemether, which is one of artemisinin-based drugs serving as antimalarial drugs, exhibits an effect on schistosomes at the immature stage and may therefore be used not only as a therapeutic drug at the early stage of infection but also for the prophylaxis of the infection, but that artemether still remains unpopular. See FIG. 1 for a life cycle of schistosomes and effective administration periods of reported existing drugs.

Even when schistosomiasis is cured by the administration of praziquantel, once one suffers from liver dysfunction, the restoration is difficult and liver dysfunction is accumulated through repetitive infections. In Japan, as mentioned above, *Schistosoma japonicum* in the country was able to be eradicated by the prevention of infection from *Oncomelania nosophora* as an intermediate host for schistosomes and the early detection and treatment of patients. In contrast, wide infected areas remain in, for example, China, Southeast Asia, and Africa, and reports on the occurrence of resistance to praziquantel also exist. There is no prophylactic means such as a vaccine at present. Accordingly, there is also an international demand for the development of a novel antischistosomal agent which may also serve as a prophylactic drug.

[Non Patent Literature 1] http://idsc.nih.go.jp/idwr/kansen/k06/k06_41/k06_41.html
[Non Patent Literature 2] Prescription Drug Package Insert: praziquantel formulation (Biltricide® tablet) manufactured and sold by Bayer Yakuhin, Ltd. (revised in April, 2005)

DISCLOSURE OF THE INVENTION

Problems to be Solved by the Invention

An object of the present invention is to provide a novel antischistosomal agent, and more specifically, to provide a novel drug capable of killing schistosomes at the immature stage and inhibiting the growth of the schistosomes in vivo to prevent the development of liver dysfunction due to eggs of the schistosomes in the case of infection with the schistosomes.

Means for Solving the Problems

The inventors of the present invention have made extensive studies in order to solve the above-mentioned problem. As a result, the inventors have found that a peroxide derivative allows the inhibition of the growth of schistosomes in vivo to prevent the development of liver dysfunction due to eggs of the schistosomes even in the case of infection with the schistosomes. Thus, the present invention has been completed.

That is, the present invention includes the following:

1. a novel antischistosomal agent, comprising as an active ingredient a peroxide derivative represented by the general formula (I):

[Chem. 1]

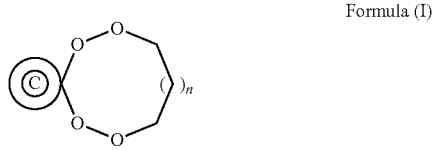

Formula (I)

[wherein, C represents an alicyclic hydrocarbon group which may be substituted, and n represents an integer of 1 to 6];

2. a novel antischistosomal agent according to the item 1, in which the peroxide derivative is a compound represented by the general formula (I) wherein C represents an alicyclic hydrocarbon group which may have a lower alkyl group as a substituent;

3. a novel antischistosomal agent according to the item 1 or 2, in which the peroxide derivative is a compound represented by the general formula (I) wherein C represents a 4-tert-butylcyclohexylidene, cyclododecylidene, oradamantylidene group, and n represents an integer of 1 to 4; and 4. a novel antischistosomal agent according to any one of the items 1 to 3, wherein the peroxide derivative is a compound represented by the following formula (II):

[Chem. 2]

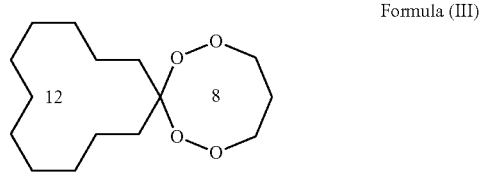

Formula (III)

Advantageous Effects of Invention

The administration of the novel antischistosomal agent of the present invention on Week 2 (during the second week) after infection with schistosomes leads to a decrease in the number of schistosomes in vivo, and the administration of the novel antischistosomal agent prior to Week 6 (the sixth week) after the infection can reduce the egg production capacity of schistosomes. Thus, the drug of the present invention can be administered to humans probably at high risk of infection with schistosomes prior to the symptom onset so as to prevent schistosomiasis and thereby avoid liver dysfunction (liver damage).

BEST MODE FOR CARRYING OUT THE INVENTION

Figure 1:
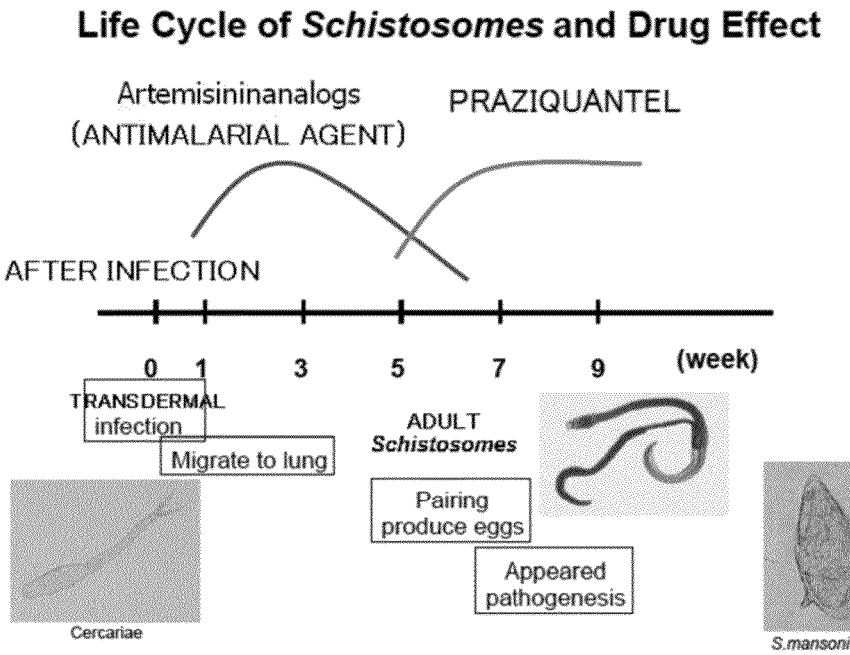
FIG. 1 is a diagram illustrating a life cycle of schistosomes and effective administration periods of existing drugs.

A novel antischistosomal agent of the present invention may be administered to individuals suspected of infection with schistosomes. Here, a number of kinds of schistosomes are known as described in the section of "Background Art" above. The schistosomes are not particularly limited in the present invention, and preferred examples thereof include *Schistosoma japonicum* and *Schistosoma mansoni*. Regarding the antischistosomal agent of the present invention, dosage schedules depending on the life cycle of schistosomes are considered. For example, the administration of the antischistosomal agent on Weeks 1 to 2 after infection leads to a decrease in the number of schistosomes in vivo and the weekly administration of the antischistosomal agent on Weeks 5 to 7 after the infection, in particular, the administration of the antischistosomal agent on Week 5 reduces the egg production capacity of schistosomes. The individuals suspected of infection with schistosomes refer to, for example, individuals who have ever been to fresh water regions at risk of infection. Even when symptoms due to infection with schistosomes are not clearly manifested, the exacerbation of the symptoms due to infection can be prevented in advance by the administration of the antischistosomal agent of the present invention.

The novel antischistosomal agent of the present invention comprises as an active ingredient a peroxide derivative represented by the following formula (I):

[Chem. 1]

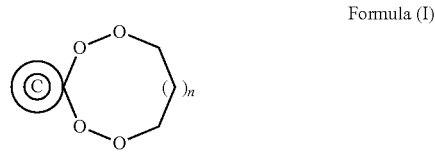

Formula (I)

[in the formula, C represents an alicyclic hydrocarbon ring group which may have a substituent, and n represents an integer of 1 to 6].

In the above-mentioned general formula (I), examples of the alicyclic hydrocarbon ring group which may have a substituent represented by C include: monocyclic alicyclic hydrocarbon groups having 3 to 12 carbon atoms such as cyclopropylidene, cyclobutylidene, cyclopentylidene, cyclohexylidene, cycloheptylidene, cyclooctylidene, cyclononylidene, cyclodecylidene, cycloundecylidene, and cyclododecylidene groups; and bridged ring or polycyclic alicyclic hydrocarbon groups such as bicyclobutylidene, bicyclooctylidene, bicyclononylidene, norbornylidene, norborenylidene, adamantylidene, and noradamantylidene groups. Of those, monocyclic alicyclic hydrocarbon groups having 6 to 12 carbon atoms or an adamantylidene group is preferred, and a cyclohexylidene, cyclododecylidene, or adamantylidene group is more preferred. Further, examples of the substituent which may be possessed by the alicyclic hydrocarbon group represented by C include: linear or branched lower alkyl groups having 1 to 6 carbon atoms such as methyl, ethyl, n-propyl, i-propyl, n-butyl, i-butyl, sec-butyl, tert-butyl or a linear or branched pentyl group; and linear or branched lower alkoxy groups having 1 to 6 carbon atoms such as methoxy, ethoxy, n-propoxy, i-propoxy, n-butoxy, i-butoxy, sec-butoxy, tert-butoxy or a linear or branched pentyloxy group. Of those, lower alkyl groups are preferred and a tert-butyl group is more preferred. Of the compounds of the present invention, a preferred compound is a compound represented by the general formula (I), wherein C represents an alicyclic hydrocarbon group which may have a lower alkyl group as a substituent, and amore preferred compound is a compound represented by the general formula (I), wherein C represents a 4-tert-butylcyclohexylidene, cyclododecylidene, oradamantylidene group, and n represents an integer of 1 to 4.

Hereinafter, embodiments of the present invention are described in detail. The peroxide derivative represented by the above-mentioned general formula (I) may be manufactured by the method described in JP 2000-229965 A.

Specifically, the peroxide derivative is manufactured by the following method:

[Chem. 3]

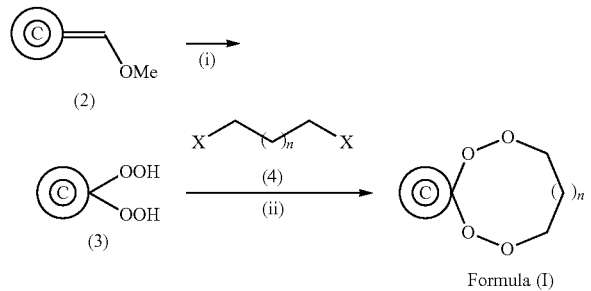

Formula (I)

[in the formula, C and n have the same meanings as those described above, and X represents a halogen atom].

In the above-mentioned reaction scheme, the halogen atom indicated by X is a fluorine atom, a chlorine atom, a bromine atom, or an iodine atom, preferably a bromine atom or an iodine atom.

<Reaction Step (i)>

This reaction step is performed in accordance with the method described in J. Org. Chem., 62, 4949 (1997). In other words, a known compound (2) is allowed to react with ozone in an appropriate solvent in the presence of hydrogen peroxide to afford a bishydroperoxide compound indicated by (3). The solvent to be used in this step is not particularly limited as long as the solvent is not involved in the reaction. Examples of the solvent include an ether, tetrahydrofuran, and acetonitrile. Of those, an ether is preferred. 30 to 100% hydrogen peroxide may be used. In the reaction, hydrogen peroxide is used in a 1- to 10-fold molar amount, preferably a 1- to 3-fold molar amount with respect to the compound (2), and ozone is used in a 0.5- to 5-fold molar amount, preferably a 1- to 2-fold molar amount with respect to the compound (2). The reaction temperature is −70 to 20° C., and the reaction time is 5 to 30 minutes. The resultant compound (3) may be easily isolated and purified from a reaction mixture by general separation means such as column chromatography and recrystallization. The compound (3) obtained in the above-mentioned reaction step (i) may be isolated or not isolated and then used in the reaction step (ii).

<Reaction Step (ii)>

The compounds represented by the compounds (3) and (4) obtained in the above-mentioned reaction step (i) are allowed to react with each other in an appropriate solvent in the presence of a base to afford a compound of the present invention represented by the general formula (I). Examples of the base to be used in this step include: alkali metal hydroxides such as potassium hydroxide, sodium hydroxide, and cesium hydroxide; alkali metal alkoxides such as sodium methoxide and sodium ethoxide; and tertiary amines such as triethylamine and diisopropylethylamine. Of those, cesium hydroxide is preferred. The solvent is not particularly limited as long as the solvent is a nonaqueous solvent, but is particularly preferably a high polar solvent such as dimethylformamide or dimethylsulfoxide. Further, each of crown ethers such as 18-crown-6 may also be added as a reaction promoter. In the reaction, each of the compound (4) and the base is used in a 1- to 3-fold molar amount with respect to the compound (3). When a reaction promoter is used, it is added in a 1- to 10-fold molar amount with respect to the compound (3). The reaction temperature is 0 to 50° C., preferably 10 to 30° C., and the reaction time is 1 to 48 hours. The resultant compound (I) may be easily isolated and purified from a reaction mixture by general separation means such as column chromatography or recrystallization.

Specific examples of the peroxide derivative contained in the novel antischistosomal agent of the present invention include compounds shown in Table 1. Those compounds may be manufactured by the method described in each of working Examples of JP 2000-229965 A. The peroxide derivative contained in the novel antischistosomal agent of the present invention is most preferably the compound (1,2,6,7-tetraoxaspiro[7.11]nonadecane) represented by the following formula (II).

TABLE 1

| 1,2,6,7-Tetraoxaspiro[7.11] nonadecane | 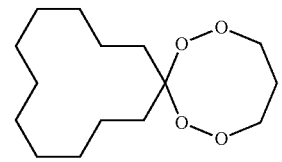 |
|---|---|
| | Formula (II) |
| 1,2,6,7-Tetraoxaspiro[8.11] icosane | 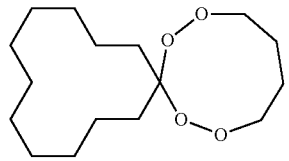 [SMILES: C1CCCCCC2(CCCCC1)OOCCCCOO2] |
| 1,2,6,7-Tetraoxaspiro[9.11] henicosane | 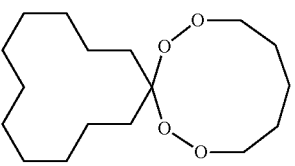 [SMILES: C1CCCCCC2(CCCCC1)OOCCCCCOO2] |

TABLE 1-continued

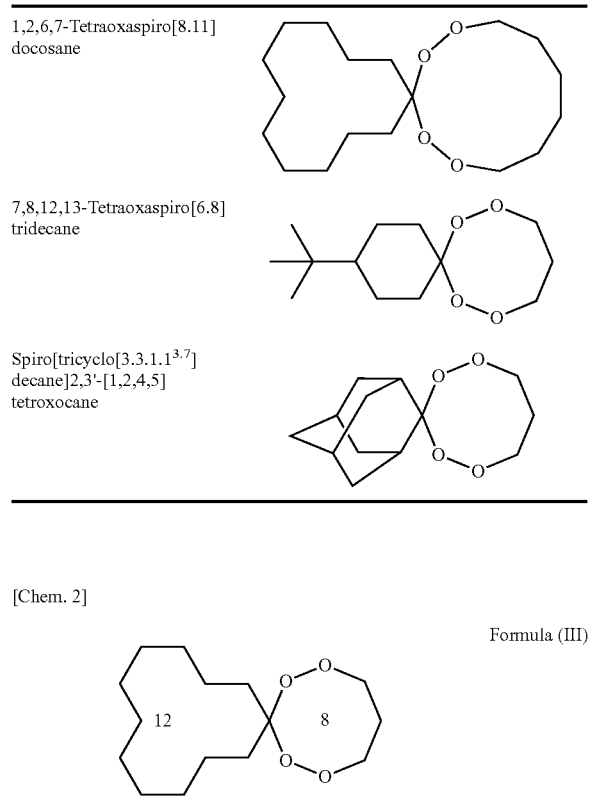

1,2,6,7-Tetraoxaspiro[8.11]
docosane 7,8,12,13-Tetraoxaspiro[6.8]
tridecane

Spiro[tricyclo[3.3.1.1$^{3.7}$]
decane]2,3'-[1,2,4,5]
tetroxocane

[Chem. 2]

Formula (III)

The novel antischistosomal agent of the present invention may be administered through any route such as oral administration, subcutaneous injection, intravenous injection, or topical administration. Further, the novel antischistosomal agent may be formulated into oral formulations such as powders, tablets, fine granules, pills, capsules, and granules, and parenteral formulations such as ophthalmic solutions, injections, and suppositories, which are generally manufactured using pharmaceutically acceptable carrier, excipient, and other additives. Examples of the pharmaceutically acceptable carrier, excipient, and other additives include glucose, lactose, gelatin, mannitol, starch paste, magnesium trisilicate, corn starch, keratin, and colloidal silica. Additional examples thereof include aids such as a stabilizer, a bulking agent, a colorant, and a fragrance. Each of those formulations may be manufactured by a known conventional manufacturing method by a person skilled in the art. The blending amount of the peroxide compound as the active ingredient contained in the novel antischistosomal agent of the present invention is preferably 0.1 to 100% by weight, more preferably 0.1 to 80% by weight, suitably 0.1 to 50% by weight. Although the daily dose cannot be generally determined because the dosage varies depending on, for example, the symptom, body weight, age, and gender of a patient, it is preferably administered at a dosage of generally 0.1 to 1,000 mg, preferably 1 to 600 mg per day for an adult human in one portion or about two to four divided portions.

EXAMPLES

Hereinafter, effects in the case of administration of the novel antischistosomal agent of the present invention are described by way of examples. It goes without saying that the present invention is not limited to the description of the examples.

Example 1

Preparation of Novel Antischistosomal Agent of Present Invention

The novel antischistosomal agent of the present invention was prepared by dissolving 120 mg of a peroxide derivative (1,2,6,7-tetraoxaspiro[7.11]nonadecane, formula (II)) obtained by synthesis according to the method described in Example 1 of JP 2000-229965 A in 2 ml of olive oil.

[Chem. 2]

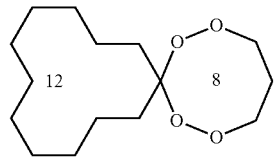

Formula (III)

Experimental Example 1

Number of Schistosomes In Vivo

Figure 2:
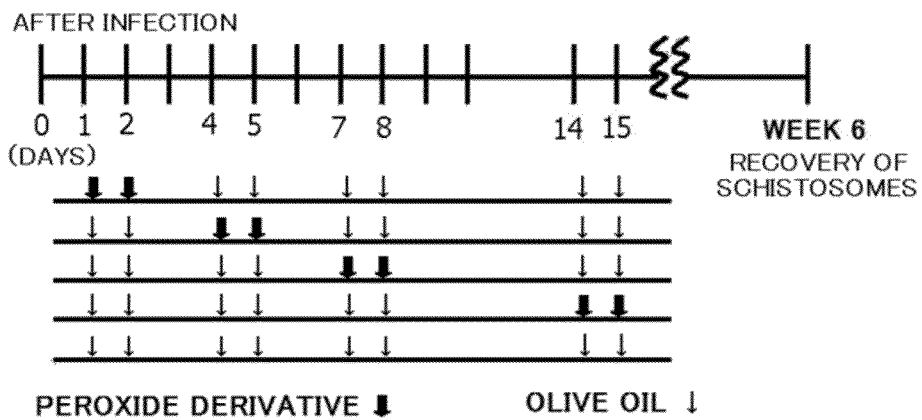
FIG. 2 is a diagram illustrating a drug dosage regimen to examine an influence of a novel antischistosomal agent of the present invention on the number of schistosomes (Experimental Example 1).

100 µl of the antischistosomal agent of the present invention were orally administered to mice (BALB/c mice, 5-week-old) infected with schistosomes (*Schistosoma mansoni*) in accordance with a drug dosage regimen of FIG. 2. As a control, 100 µl of olive oil was administered. On Week 6 after the infection, the mice were sacrificed with an overdose of anesthetic, and the number of schistosomes recovered was counted under a microscope.

Figure 3:
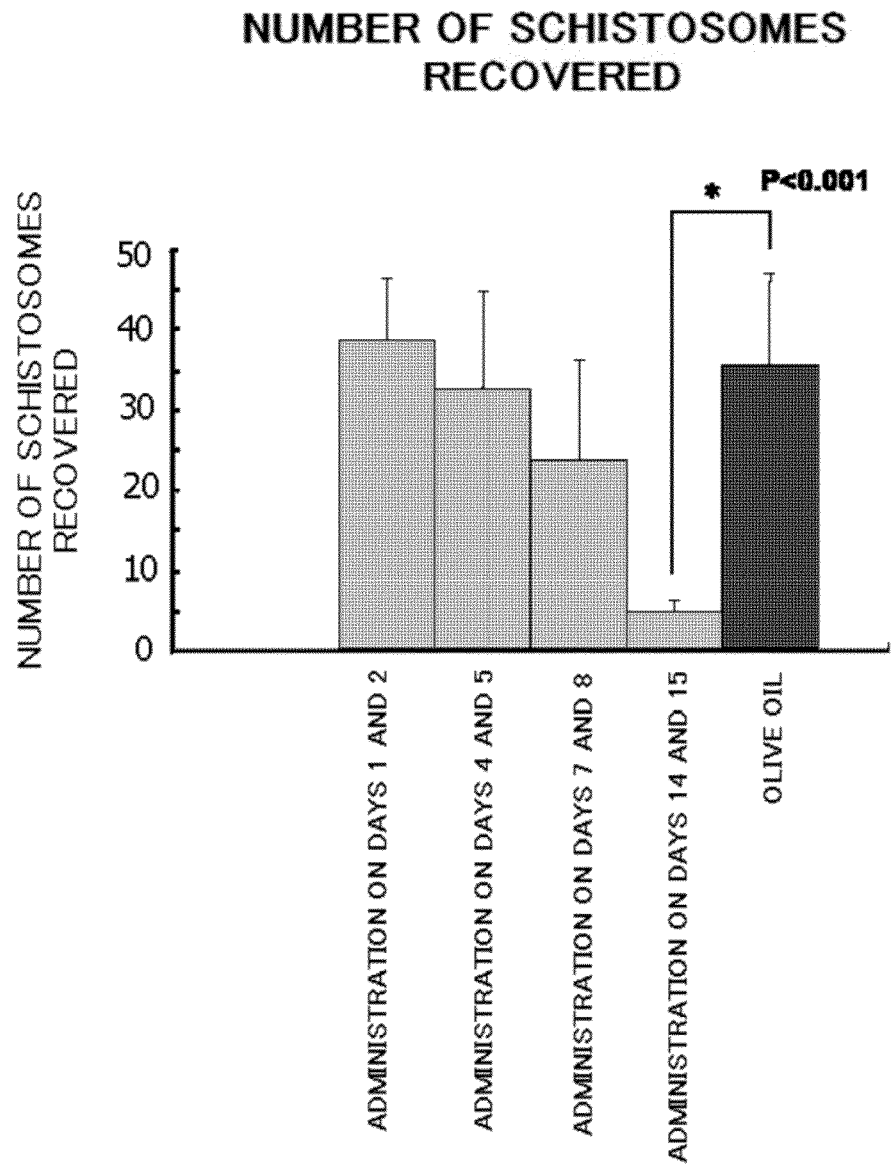
FIG. 3 is a graph illustrating an influence of the novel antischistosomal agent of the present invention on the number of schistosomes (Experimental Example 1).

The results confirmed that the number of schistosomes in a group in which the antischistosomal agent was administered on Days 14 and 15 after the infection was smaller as compared to that in a group in which the antischistosomal agent was administered immediately after the infection, and was reduced by 86% as compared to the olive oil administration group as a control (FIG. 3).

Experimental Example 2

Number of Eggs Produced Per Adult Female Schistosome

Figure 4:
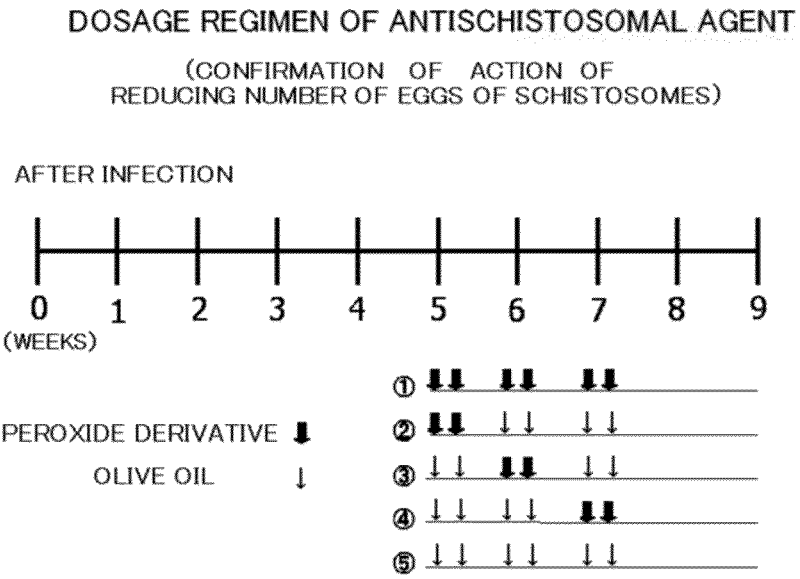
FIG. 4 is a diagram illustrating a drug dosage regimen to examine an influence of the novel antischistosomal agent of the present invention on the number of eggs produced (Experimental Example 2).

100 µl of the antischistosomal agent of the present invention were orally administered to mice (BALB/c mice, 5-week-old) infected with schistosomes (*Schistosoma mansoni*) in accordance with a drug dosage regimen of FIG. 4. As a control, 100 µl of olive oil was administered. On Week 9 after the infection, the mice were sacrificed with an overdose of anesthetic, and the number of schistosomes recovered and the number of eggs produced per adult female schistosome were measured. The number of schistosomes was measured in the same manner as in Experimental Example 1, and the number of eggs produced was also counted under a microscope.

Figure 5:
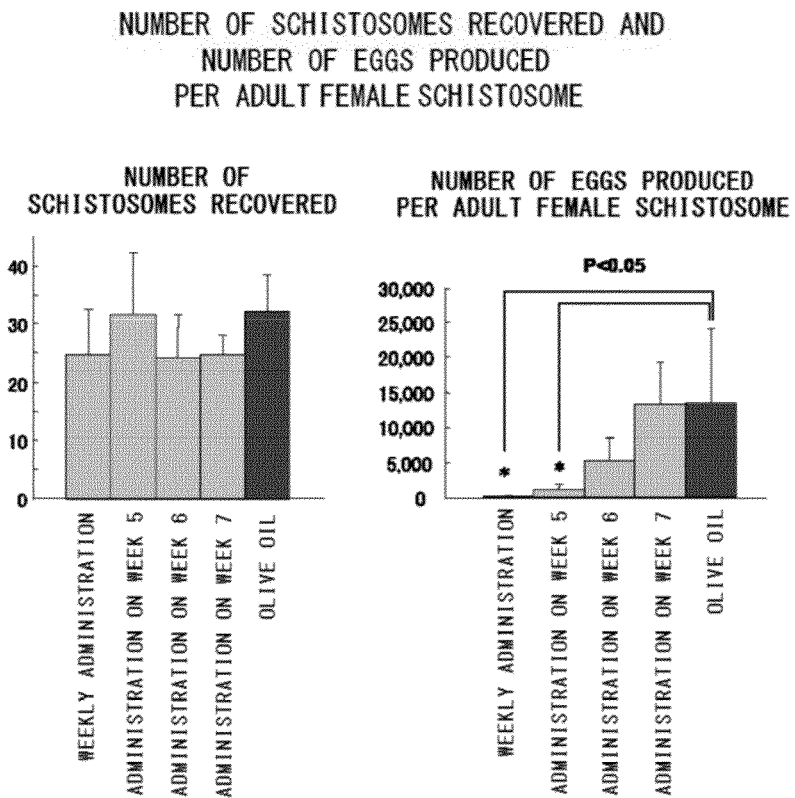
FIG. 5 are graphs illustrating influences of the novel antischistosomal agent of the present invention on the number of eggs produced (Experimental Example 2).

The results confirmed that the number of schistosomes in the case of administration of the antischistosomal agent on each of Weeks 5 to 7 after the infection was not significantly reduced as compared to that in the olive oil administration group as a control, whereas the number of eggs produced per adult female schistosome was reduced by 98% as compared to that in the olive oil administration group. Also in the case of administration on Week 5 only after the infection, the number of eggs produced was reduced by 87% (FIG. 5).

Experimental Example 3

Macroscopic Findings on Liver Lesions in Schistosome-Infected Mice

Figure 6:
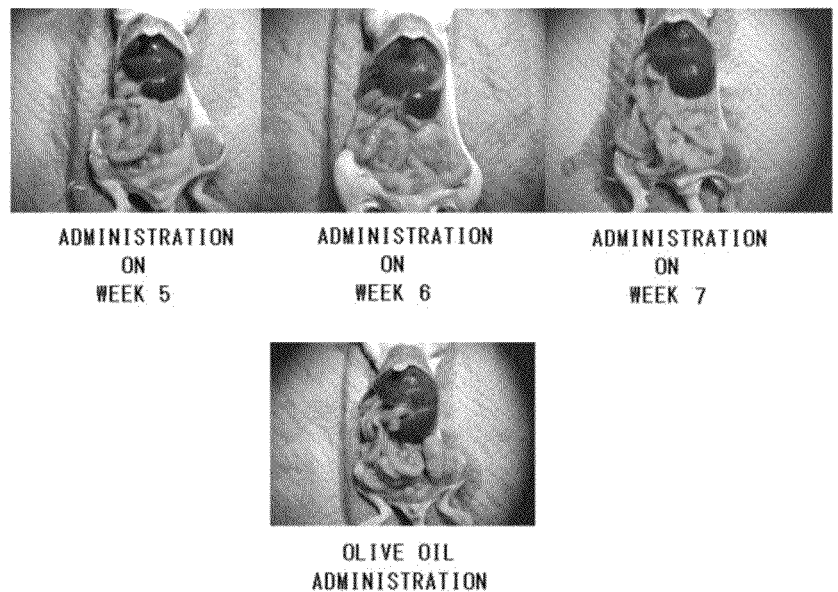
FIG. 6 are photographs showing influences of the novel antischistosomal agent of the present invention on liver lesions of schistosome-infected mice (Experimental Example 3).

Viscera of each of the mice of Experimental Example 2 were observed macroscopically. As a result, liver lesions due to eggs of schistosomes were observed in the olive oil administration group, whereas few liver lesions were observed in the group in which the antischistosomal agent of the present invention was administered on Week 5 after the infection (FIG. 6). Further, enlargement of spleen was also inhibited. The results also confirmed that the antischistosomal agent of the present invention was effective on liver lesions caused by eggs of schistosomes as well.

Figure 7:
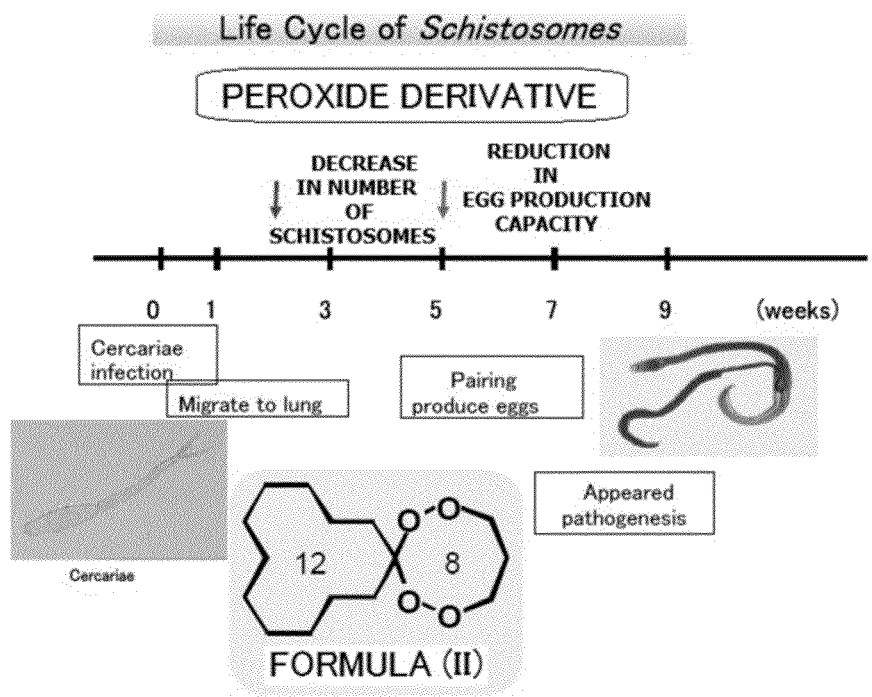
FIG. 7 is a diagram illustrating a life cycle of schistosomes and an effective administration period of the novel antischistosomal agent of the present invention.

As described above, the administration of the antischistosomal agent of the present invention on Week 2 after the infection led to a decrease in the number of schistosomes, and the administration of the antischistosomal agent on Week 5 after the infection led to a significant decrease in the number of eggs produced per adult female schistosome. Based on those results, a life cycle of schistosomes and effects depending on a dosage schedule of the antischistosomal agent of the present invention were summarized in FIG. 7. The results confirmed that the administration of the antischistosomal agent of the present invention enabled the reduction in the number of schistosomes and also the reduction in the number of eggs produced, prior to the development of liver lesions due to schistosomes. It has been confirmed that the antischistosomal agent of the present invention can be prophylactically administered to individuals at risk of infection with schistosomes.

INDUSTRIAL APPLICABILITY

As mentioned in detail above, the administration of the novel antischistosomal agent of the present invention on Week 2 after infection with schistosomes leads to a decrease in the number of schistosomes in a living body, and the administration of the novel antischistosomal agent prior to Week 6 after the infection leads to a reduction in egg production capacity of schistosomes. Thus, the drug of the present invention, when administered to humans probably at high risk of infection with schistosomes in accordance with the above-mentioned dosage regimen, can inhibit schistosomiasis and prevent the development of liver dysfunction. Accordingly, the novel antischistosomal agent of the present invention can be utilized as an excellent drug which may be prophylactically administered to individuals at risk of infection with schistosomes.

The invention claimed is:

1. A method for treating schistosomiasis comprising administering to a patient a composition comprising a peroxide derivative represented by the general formula (I):

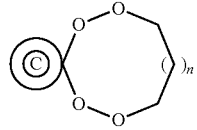

Formula (I)

wherein C represents a monocyclic alicyclic hydrocarbon group having 3 to 12 carbon atoms or an adamantylidene group, which optionally has a linear or branched lower alkyl group having 1 to 6 carbon atoms as a substituent, and n represents an integer of 1 to 6.

2. The method according to claim 1, wherein C represents a 4-tert-butylcyclohexylidene, cyclododecylidene, or adamantylidene group, and n represents an integer of 1 to 4.

3. The method according to claim 1, wherein the peroxide derivative is a compound represented by the following formula (II):

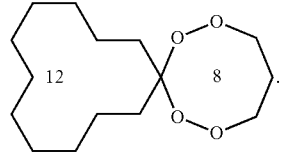

Formula (III)

4. A method for treating schistosomiasis comprising administering to a patient a composition comprising a peroxide derivative represented by the general formula (I), wherein the peroxide derivative is administered two or four times a week at a dosage of 1 to 1,000 mg on any one or a plurality of weeks selected from weeks 2 to 7 after infection with schistosomes:

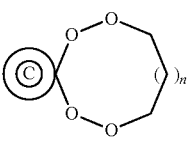

Formula (I)

wherein C represents a monocyclic alicyclic hydrocarbon group having 3 to 12 carbon atoms or an adamantylidene group, which optionally has a linear or branched lower alkyl group having 1 to 6 carbon atoms as a substituent, and n represents an integer of 1 to 6.

5. The method according to claim 4, wherein the peroxide derivative is administered two or four times a week at a dosage of 1 to 1,000 mg on weeks 2 and/or 5 after infection with schistosomes.

6. The method according to claim 4, wherein the peroxide derivative is administered two or four times at a dosage of 1 to 1,000 mg on week 5 after infection with schistosomes.

7. The method according to claim 4, wherein C represents a 4-tert-butylcyclohexylidene, cyclododecylidene, or adamantylidene group, and n represents an integer of 1 to 4.

8. The method according to claim 4, wherein the peroxide derivative is a compound represented by the following formula (II):

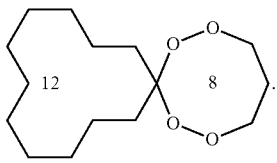

Formula (III)

9. The method according to claim 1, wherein the further comprises olive oil.

10. The method according to claim 9, wherein the composition comprises the peroxide derivative in a blending ratio of 120 mg with respect to 2 ml of the olive oil.

11. The method of claim 1, wherein said schistosomiasis is urogenital schistosomiasis.

12. The method of claim 1, wherein said schistosomiasis is intestinal schistosomiasis.

13. The method of claim 1, wherein said treating comprises killing schistosomes.

14. The method of claim 1, wherein said treating comprises killing schistosomes at an immature stage and inhibiting growth of the schistosomes in vivo.

15. The method of claim 1, wherein said treating comprises killing schistosomes at an immature stage and inhibiting growth of the schistosomes in vivo to prevent the development of liver dysfunction due to eggs of the schistosomes in the case of infection with the schistosomes.

16. The method of claim 4, wherein said schistosomiasis is urogenital schistosomiasis.

17. The method of claim 4, wherein said schistosomiasis is intestinal schistosomiasis.

18. The method of claim 4, wherein said treating comprises killing schistosomes.

19. The method of claim 4, wherein said treating comprises killing schistosomes at an immature stage and inhibiting growth of the schistosomes in vivo.

20. The method of claim 4, wherein said treating comprises killing schistosomes at an immature stage and inhibiting growth of the schistosomes in vivo to prevent the development of liver dysfunction due to eggs of the schistosomes in the case of infection with the schistosomes.

* * * * *